United States Patent [19]

Franzl

[11] 4,103,682

[45] Aug. 1, 1978

[54] ANATOMICAL DIGIT AND APPENDAGE-IMMOBILIZING DEVICE

[76] Inventor: Gertrude K. Franzl, 105-25 65th Ave., Forest Hills, New York, N.Y. 11375

[21] Appl. No.: 724,713

[22] Filed: Sep. 20, 1976

[51] Int. Cl.² .............................................. A61F 5/04
[52] U.S. Cl. ..................................... 128/87 A; 128/77
[58] Field of Search .................. 128/87 A, 87 R, 77, 128/89

[56] References Cited

U.S. PATENT DOCUMENTS

| | | | |
|---|---|---|---|
| 1,837,691 | 12/1931 | Thigpen | 128/87 A |
| 2,022,883 | 12/1935 | Gee | 128/87 A |
| 2,072,683 | 3/1937 | Niedorff | 128/77 |
| 2,273,028 | 2/1942 | Eaton | 128/87 A |
| 2,646,794 | 7/1953 | Baer | 128/87 A |
| 2,863,449 | 12/1958 | Spencer | 128/87 A |
| 3,307,537 | 3/1967 | Simon et al. | 128/90 |
| 3,692,022 | 9/1972 | Ewing | 128/87 A |

FOREIGN PATENT DOCUMENTS

| | | | |
|---|---|---|---|
| 381,055 | 12/1907 | France | 128/77 |
| 270,341 | 9/1913 | Fed. Rep. of Germany | 128/87 A |

*Primary Examiner*—John D. Yasko

*Attorney, Agent, or Firm*—John J. Posta, Jr.

[57] ABSTRACT

The improved device of the present invention immobilizes anatomical digits and, when needed, appendages in an improved, light weight, simplified, inexpensive, comfortable and effective way. It comprises a generally open one sided mold conforming to a major surface of at least one digit. It extends the length of the digit and past the point of connection between the appendage bearing the digit and the limb to which the appendage is connected.

Several spaced securing means connected to the mold adjacent opposite ends thereof releasably secure it to the digit and to either the appendage or limb. The mold preferably is perforated and lined with a soft non-allergenic material. It may be adjustable as to length and/or width so as to be adaptable to various sized digits (fingers or toes) and appendages (hands or feet).

One of the securing means may be a band containing a pocket to receive the end of the mold adjacent the appendage-limb junction. The device is particularly useful in effectively immobilizing arthritic digits and appendages without in any way interfering with the normal use of unaffected adjacent digits and appendages.

2 Claims, 10 Drawing Figures

ANATOMICAL DIGIT AND APPENDAGE-IMMOBILIZING DEVICE

BACKGROUND OF THE INVENTION

1. Field of the Invention

The present invention relates generally to medical devices and more particularly to light weight open sided molds particularly adapted for immobilizing digits and appendages of arthritics, among others.

2. Prior Art

It is well known that there are two main forms of arthritis, called osteoarthritis (degenerative joint disease) and rheumatoid arthritis. Both forms of the disease, although they may be due to different causes, exhibit similar symptoms. Thus, in the active form of each disease calcium is removed from the affected joints and other areas and is redeposited in and around the joints in an irregular tissue-inflaming pattern.

The inflamed tissue swells, whereupon movements of the joints very difficult and very painful. The tissue inflammation in turn appears to stimulate the body to attempt to seal off the area by further calcium redeposition, which leads to further tissue inflammation, and the cycle continues. The cycle can only be broken by reducing tissue inflammation with such anti-pyretic medicines as cortisone, sodium acetyl salicylate, phenoxy butogene and related compounds. Most often, the joints of the fingers and toes are affected.

In certain of such instances temporary immobilization of the affected joints is preferred or required to help prevent further tissue irritation, and to reduce pain and swelling, which can be very considerable. Such immobilization is ordinarily accomplished either by winding many turns of elastic bandages tightly around the affected joints or by applying plaster splints and casts and the like to wholly enclose the affected joint areas. In both such instances, not only are the affected joints sealed in so that they tend to undesirably retain heat, but they are encased in and pressed painfully upon by unsightly, bulky coverings in such a way as to interfere with the normal movement and function of adjacent unaffected body parts, such as digits.

Accordingly, there is a need for a simple, attractive, compact, light weight joint immobilizing means which will permit the free circulation of air to and transfer of heat from the affected joints and which will not interfere with the normal use of adjacent parts, such as digits.

SUMMARY OF THE INVENTION

The foregoing needs have been satisfied by the improved digit and appendage-immobilizing device of the present invention. The device is simple, inexpensive, durable, attractive to view and easy to use and reuse, light in weight, comfortable and cool to wear, permitting the rapid dissipation of heat from the covered joints, and does not in any way interfere with the normal use of adjacent unaffected digits and appendages.

The device comprises a one sided porous mold conforming in shape to a major surface of at least one digit and extending the full length of that digit plus a distance necessary to cause it to pass the point of connection between the appendage bearing the digit and the limb to which the appendage is connected.

The device includes securing means connected to the mold for releasably securing the mold to the digit and to either the appendage or associated limb. The mold may be lined with non-allergenic material and may be adjustable in length and/or width.

Moreover, the securing means adjacent the appendage-limb junction end of the mold may include a pocket to receive that end in a convenient comfortable manner.

The mold may be of wood, or other cellulosic material, plastic, plaster, wire screening metal or the like and can be colored and/or texturized to resemble the surfaces to which it is applied, so as to provide an improved cosmetic appearance. Further advantages are set forth in the following detailed description and accompanying drawings.

DRAWINGS

Figure 1:
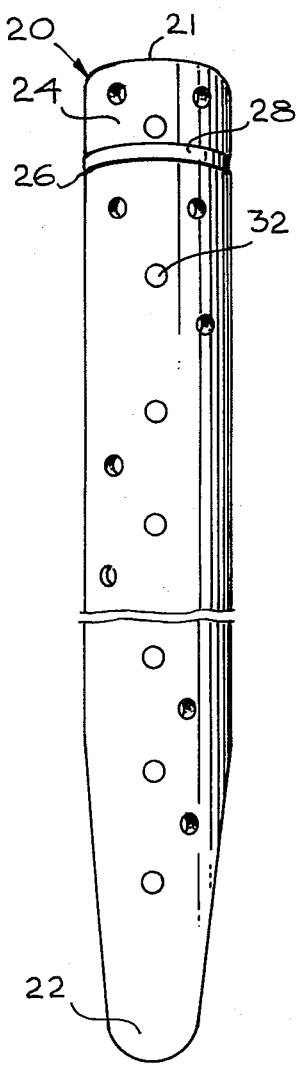
FIG. 1 is a schematic top plan view of a first preferred embodiment of a mold for the improved immobilizing device of the present invention, adapted for use on a single digit.
Figure 2:
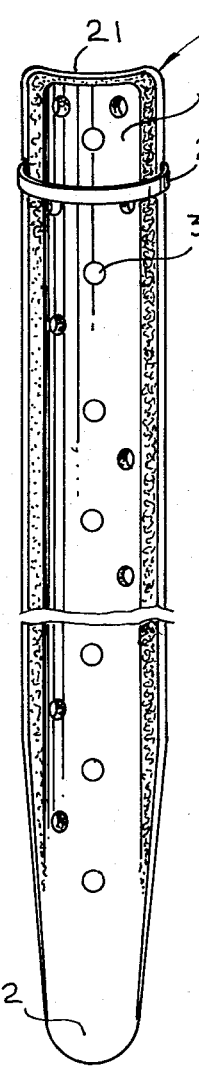
FIG. 2 is a schematic bottom plan view of the mold of FIG. 1.

FIGS. 1 and 2

Now referring more particularly to FIG. 1, a mold 20 is shown in top plan view. By the term mold as used herein is meant a shell which generally conforms to the contours of at least a portion of the surface of a hand or foot, but which may or may not have been formed by molding.

Thus, mold 20 comprises a shell 21 which is then, e.g., $\frac{1}{8}$ inch - $\frac{1}{4}$ inch thick, of a width, for example, to span the width of an adult finger, e.g., $\frac{3}{4}$ inch - 1 inch, and of a length to extend the full length of the finger and along the hand to and past the wrist, e.g., 7 inches - 9 inches.

Shell 21 can be fabricated in any suitable manner, as previously indicated, e.g., of wood, metal, plastic, cellulose, wire screening, etc., and should be stiff enough to resist bending. It is roughly triangular or wedge shaped, with its narrower end 22 to the rear.

Its front end 24 bears a groove 26 disposed ahead of the first finger joint and within which groove an elastic circular band 28 releasably resides for releasably securing end 24 to a finger (not shown). Shell 21 is designed to closely conform to the dorsal surface of a digit, specifically a finger.

Now referring more particularly to FIG. 2, mold 20 is shown to include on the underside of shell 21 a layer 30 of non-allergenic synthetic or natural foam rubber or the like, as a cushion, e.g., ¼ inch thick, which layer 30 bears a plurality of holes 32 which extend through shell 21 (FIGS. 1 and 2) and which assure that mold 20 will be comfortable and cool when applied to a finger and will permit free exchange of heat and air to and from the affected joint(s) of that finger and the exterior.

Figure 3:
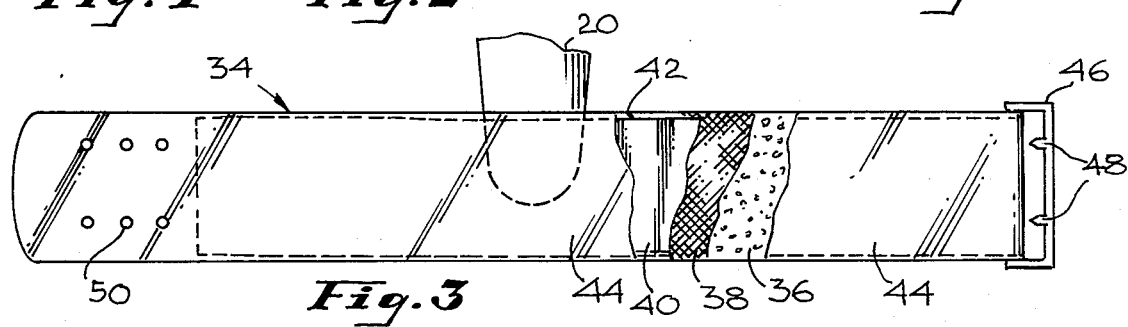
FIG. 3 is a schematic top plan view of a pocketcontaining releasable limb for the mold of FIG. 1.
Figure 4:
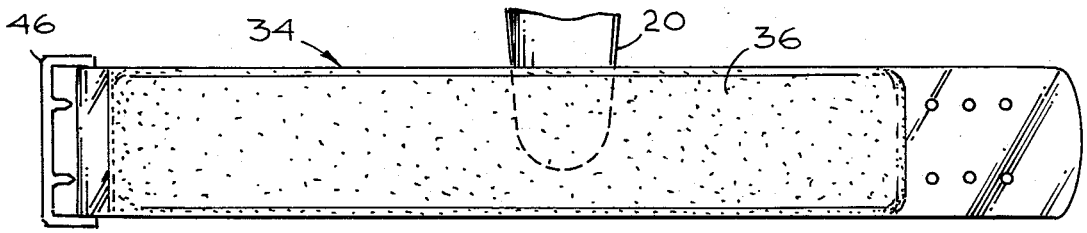
FIG. 4 is a schematic bottom plan view of the hand of FIG. 3.

FIGS. 3 and 4

End 22 of mold 20 is releasably anchored in place through the use of a detachable pocket-bearing wrist band 34 (which can be made of elastic or other material, FIGS. 3 and 4). Thus, band 34 comprises a plurality of conjoined layers of material, for example, an innermost layer 36 which may be of non-allergenic foam rubber or the like, a second layer 38 of cloth, leather or the like secured thereto, as by sticking, a third layer 40 forming an open topped closed bottom pocket 42 and a fourth layer 44 overlying layer 40 and pocket 42. Layers 40 and 44 may also be of leather, cloth, etc.

Layer 44 is provided with a buckle 46 with prongs 48 at one end thereof and a plurality of spaced holes 50 at the opposite end thereof for releasable engagement with prongs 48 to releasably bind hand 34 around the wrist or ankle.

As shown in FIGS. 3 and 4, end 22 of mold 20 is releasably disposed in pocket 42 so as to hold mold 20 in the proper position relative to a wrist, hand and finger (not shown).

FIG. 5

Figure 5:
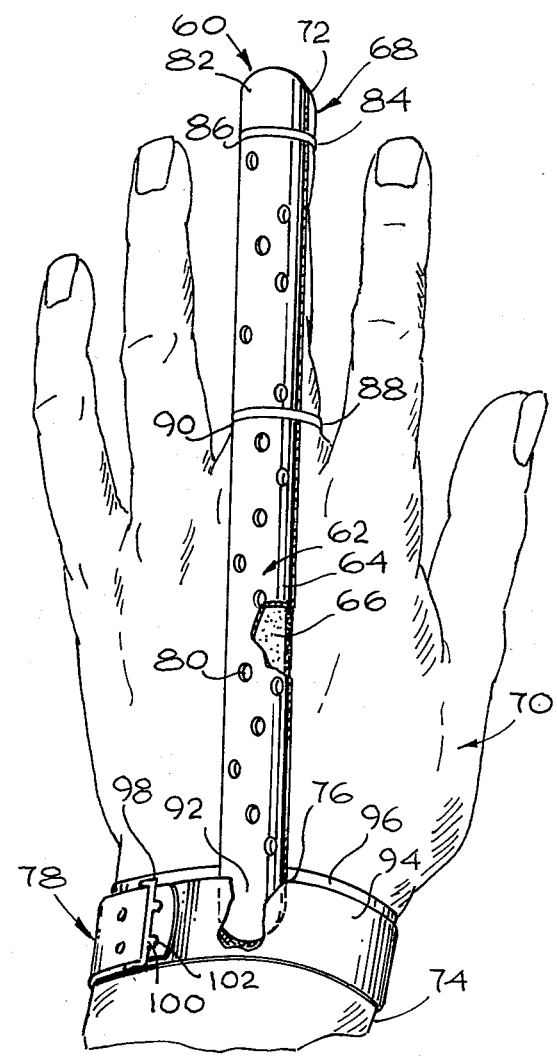
FIG. 5 is a schematic top plan view of a second preferred embodiment of the improved immobilizing device of the present invention in place on a human hand.

A second preferred embodiment of the improved immobilizing device of the present invention is schematically shown in FIG. 5 in top plan view. Thus, device 60 is shown which comprises a mold 62 having a stiff outer shell 64 and a soft inner lining 66. Shell 64 is elongated, extending the width of a finger 68 of the hand 70 as shown, and from the tip 72 of finger 68 along the back of hand 70 to wrist 74 and the pocket 76 of a detachable wrist strap 78. Mold 62 has a plurality of holes 80 extending therethrough so that finger 68 permits air to freely circulate thereto. Front end 82 of mold 62 is releasably secured in place on finger 68 by an elastic rubber band 84 disposed in groove 86 of mold 62 and around tip 72 of finger 68.

The mid-portion of mold 62 is held against the dorsal side of finger 68 by a similar rubber band 88 in groove 90 of mold 62 and around finger 68, while rear end 92 of mold 62 is disposed in pocket 76 formed between an outer layer 94 and an inner layer 96 of strap 78.

Strap 78 is releasably held in place via a buckle 98 at one end thereof with its prongs 100 extending through eyes 102 at the other end thereof.

It can be seen that, with device 60 in place, as shown in FIG. 5, fingers of hand 70 other than finger 68 can be freely moved and allowed to perform normal tasks, while finger 68 is totally immobilized by device 60 for arthritic relief, etc. Device 60 is cool, comfortable, small, light and attractive, easily applied, removed and reused, and of low cost and little maintenance.

FIG. 6

Figure 6:
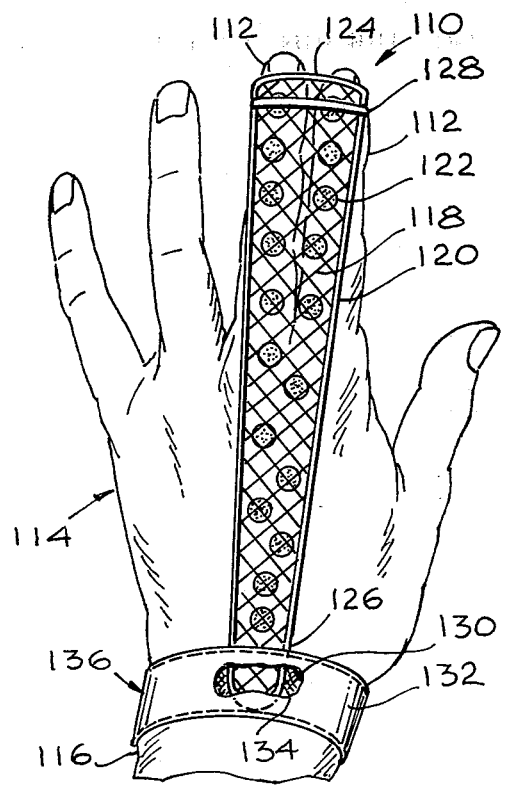
FIG. 6 is a schematic top plan view of a third preferred embodiment of the improved immobilizing device of the present invention in place on a human hand.

A third embodiment of the present invention is set forth schematically in FIG. 6. Thus, device 110 is shown, generally similar to device 60 but adapted to span two adjacent fingers 112 of hand 114 and to extend to wrist 116. Device 110 comprises an open wire screen 118 on a stiff metal frame 120. Frame 120 is backed by a plurality of spaced raised circular cushions 122 of sponge rubber which keep frame 120 from closely contacting hand 114.

Frame 120 is generally triangular, broader at the front end 124 thereof than at its rear end 126. It is releasably secured in place by an elastic rubber band 128 around front end 124 and fingers 112, and by the releasable insertion of rear end 126 in a pocket 130 formed between an outer layer 132 and inner layer 134 of a stretch wrist band 136 extending around wrist 116.

Device 110 has the advantages of device 60, immobilizing in this instance two fingers 112 while allowing the remainder of hand 114 to be freely used, thus permitting the joints of fingers 112 to readily heal.

FIG. 7

Figure 7:
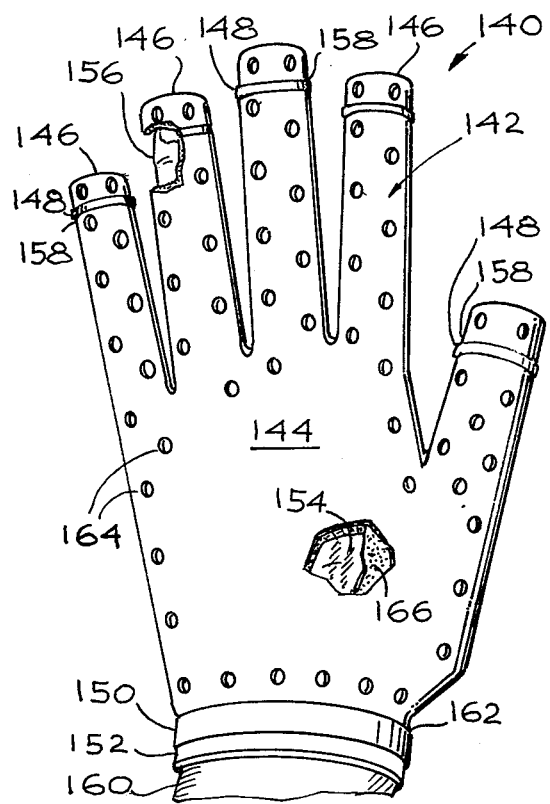
FIG. 7 is a schematic top plan view of a fourth preferred embodiment of the improved immobilizing device of the present invention in place over and entirely immobilizing a human hand.

A further version of the device of the present invention is schematically shown in FIG. 7. Thus, a device 140 is shown in top plan view, which comprises a mold 142 in the form of a hand 144 with fingers 146, and releasable attaching means in the form of a plurality of elastic bands 148 for various of fingers 146 and a large elastic band 150 for the wrist portion 152 of mold 142.

Mold 142 is shown in place over a human hand 154, releasably secured to human fingers 156 via bands 148 in grooves 158 on fingers 146 and to a human wrist 160 via band 150 in a groove 162 in wrist 152.

Mold 142 is rigid and of wood, plastic, metal or the like, perforated with holes 164 and provided with a porous lining 166 of cloth, perforated rubber or the like to keep it cool and comfortable. Device 140 totally immobilizes hand 154 and fingers 156, yet is very light, attractive, inexpensive and comfortable.

FIG. 8

Figure 8:
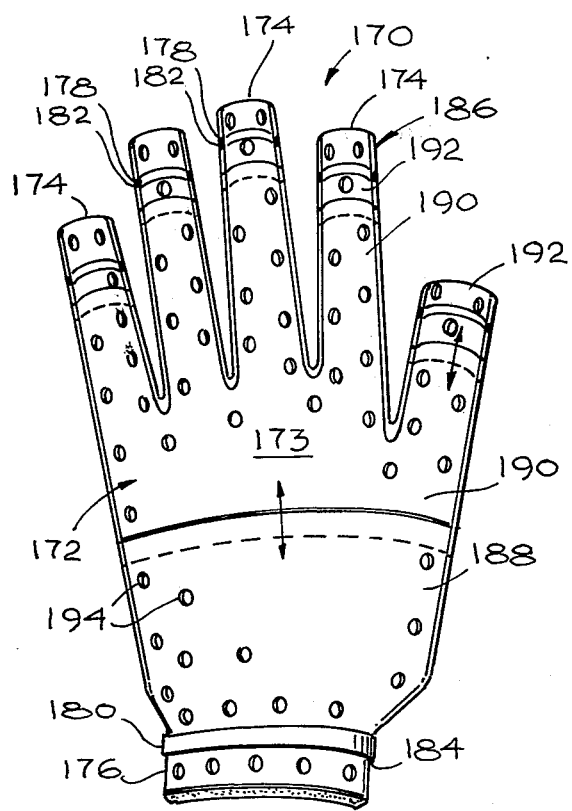
FIG. 8 is a schematic top plan view of a fifth preferred embodiment of the improved immobilizing device of the present invention, said device being adapted for adjustment longitudinally to adjust it to various sizes of human hands.

A full hand device similar to that of FIG. 7 is shown in top plan view in FIG. 8. Thus, device 170 is shown which comprises a full mold 172 in the shape of a hand 173 with fingers 174 and wrist 176, and attaching means in the form of rubber bands 178 for fingers 174 and a rubber band 180 for wrist 176. Bands 178 are in grooves 182 of fingers 174 and band 180 is in groove 184 of wrist 178.

Mold 172 includes a plurality of overlapping slideably engaged plates 186 which allow it to be adjusted longitudinally as needed, to fit the contours of an individual hand. Thus, a rear plate 188 overlaps and slideably engages a middle plate 190 which in turn overlaps and slideably engages a plurality of finger plates 192, as by a bayonet fit or other conventional arrangement. Plates 188 and 190 permit adjustment of the length of the hand 173 while plates 190 and 192 permit adjustment of the length of the fingers 174.

Mold 172 is perforated with air holes 194 and may be lined for extra comfort. Device 170 affords the advantages of device 140, plus adjustability.

It will be understood that, if desired, device 170 could be made adjustable as to width instead of, or in addition to adjustability as to length, as described.

Figure 10:
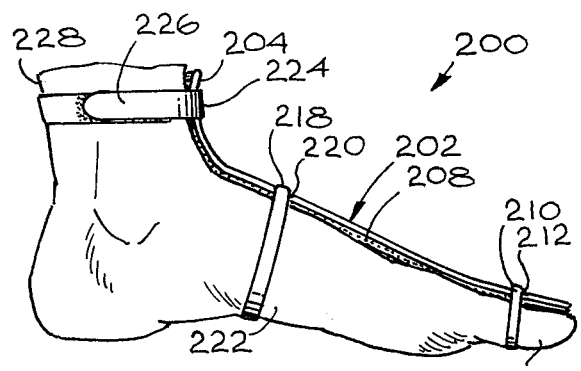
Figure 9:
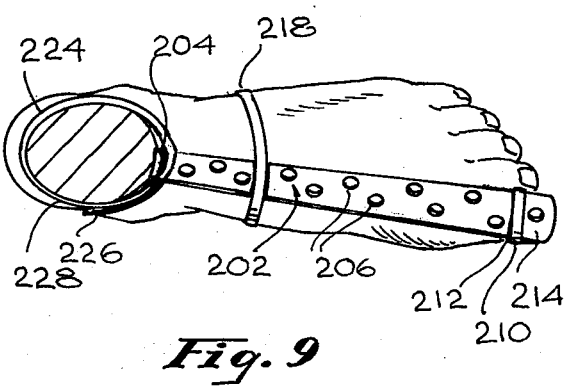
FIG. 9 is a schematic top plan view of a sixth preferred embodiment of the improved immobilizing device of the present invention in place over a human foot to immobilize a toe thereof; and, FIG. 10 is a schematic side elevation of the device of FIG. 9.

FIGS. 9 and 10

A still further embodiment of the improved device of the present invention is schematically set forth in FIGS. 9 and 10. Thus, a device 200 is shown which is adapted for use as a toe brace. Device 200 comprises a mold 202 of thin metal, wood, etc. conforming to the dorsal surface of the main (great) toe, the top of the foot and a portion of the ankle, and is of generally wedge shape with its rear end 204 reflected upwardly. Mold 202 is porous, having holes 206 therethrough, and has a soft inner lining 208 of foam rubber.

Mold 202 is releasably held in place by a first rubber band 210 in a groove 212 at the front end 214 thereof ahead of the first joint of the great toe 216 and extending around the great toe 216. It is also held in place by a second rubber band 218 in a second groove 220 at the mid-portion thereof, which band 218 extends around the instep 222, and by a third elastic band 224 which is releasably secured to itself, as at 226, and extends over the ankle 228 and rear end 204 of mold 202.

Thus, device 200 is easily fixed in place and just as easily removed, is light in weight, inexpensive and helps to immobilize the desired toe or toes, such as great toe 216, without the need for heavy, cumbersome unattractive casts, etc. Other features of this embodiment are similar to the previously described embodiments and have their advantages.

Various modifications, changes, alterations and additions can be made in the present device, its components and their parameters. All such modifications, changes, alterations and additions as are within the scope of the appended claims form part of the present invention.

What is claimed is:

1. An improved device for supporting one or more fingers, said device comprising, in combination:
   a. at least one generally rigid elongated mold adapted to generally conform to a major surface of at least one digit and extending along the length of said digit over both finger joints and terminating at and overlying the wrist;
   b. a wrist securing means including a composite band adapted to encircle the wrist;
   c. a non-allergenic layer of material secured to the underside of said mold;
   d. said mold and said layer having a plurality of aligned openings therein;
   e. a non-allergenic layer secured to the underside of said composite band;
   f. said composite band having an inner band portion and an outer band portion constructed so as to form a pocket therein;
   g. adjustable fastening means secured to both ends of said composite band;
   h. said composite band being adapted to selectively receive and frictionally, releasably retain one end of one or more of said molds therein;
   i. said adjustable fastening means adapted to be adjusted to accommodate within said pocket the ends of varying numbers of molds and further adapted to be tightened to frictionally and releasably retain said ends within the pocket of the composite band;
   j. said mold having a first groove disposed in the upper end thereof extending in a transverse direction to the length of the mold and at a location overlying the portion of a finger extending past the outermost finger joint;
   k. a first elastic band member;
   l. said first elastic band member adapted to be disposed within said first groove and encircle both said mold and the portion of a finger lying thereunder;
   m. said first groove adapted to maintain said first elastic band member in a firxed position with respect to said finger; and,
   n. whereby said molds can readily be removed from said pocket by selectively sliding them out of said pocket.

2. The improved device of claim 1 wherein said mold includes a second groove disposed therein extending in a transverse direction to the length of said mold at a location overlying that portion of the finger adjacent the knuckles of the hand;
   a. a second elastic band member adapted to be disposed within said second groove and encircle both said mold and the portion of the finger lying thereunder; and,
   b. said second groove adapted to maintain said second elastic band member in a fixed position with respect to said finger.

* * * * *